United States Patent [19]

Rosene

[11] 4,398,046

[45] Aug. 9, 1983

[54] GLYCOL PURIFICATION WITH MINIMAL PH DROP

[75] Inventor: Michael R. Rosene, Pittsburgh, Pa.

[73] Assignee: Calgon Carbon Corporation, Pittsburgh, Pa.

[21] Appl. No.: 366,439

[22] Filed: Apr. 7, 1982

[51] Int. Cl.³ ............................................. B01D 15/00
[52] U.S. Cl. .................................... 568/679; 210/679; 568/872; 568/917
[58] Field of Search ...................... 210/679, 694, 917; 252/447; 568/679, 872, 917

[56] References Cited

U.S. PATENT DOCUMENTS 2,822,304  2/1958  Gillmore et al. .................. 127/55
4,125,482  3/1977  Sinha .................................. 252/447
4,150,045  4/1978  Sinha .................................. 260/424

OTHER PUBLICATIONS

Calgon Technical Bulletin No. 23-62, "Glycol Purification with Granular Activated Carbon".
Calgon Product Specification Sheet No. 23-76, "Type Cane Cal Granular Carbon".
The Condensed Chemical Dictionary, 9th ed., Van Nostrand Reinhold Co. N.Y., 1971, p. 533.

*Primary Examiner*—Ivars C. Cintins
*Attorney, Agent, or Firm*—Martin L. Katz; R. Brent Olson; Ernest V. Linek

[57] ABSTRACT

Standard activated carbons have been commonly employed in the purification of contaminated glycol scrubbing solutions used in a liquid-liquid extraction process for the manufacture of petrochemicals. These carbons are shown to cause a depression of pH within the glycol stream when a new carbon type is installed or when the exhausted carbon is replaced. The use of a magnesite containing activated carbon minimizes this pH drop to acceptable levels.

7 Claims, No Drawings

GLYCOL PURIFICATION WITH MINIMAL PH DROP

BACKGROUND OF THE INVENTION

Standard activated carbons have been employed in the purification of contaminated glycol scrubbing solutions that are used in liquid-liquid extraction processes in the manufacture of petrochemicals. See for example, *Technical Bulletin* No. 23-62, copyright 1978, Calgon Corporation, Pittsburgh, Pa., which is herein incorporated by reference.

The use of standard activated carbons in a glycol scrubbing solution purification system causes an unacceptable depression of pH within the glycol stream when a new carbon supply is installed or when the exhausted carbon is changed. This pH drop is undesirable because isotherms indicate that carbon adsorptive capacity for colored impurities from a glycol scrubbing solution is best at high pH ($\geq 6$).

It has been discovered that this pH drop is reduced when an activated carbon containing magnesite is employed.

SUMMARY OF THE INVENTION

This invention reduces the pH drop associated with either a change in carbon type or the installation of a fresh carbon supply in the purification of contaminated glycol scrubbing solutions used in liquid-liquid extractions for the manfacture of petrochemicals.

There is thus provided an improvement in the method of purifying contaminated glycol scrubbing solutions used in a liquid-liquid extraction process for the manufacture of petrochemicals by passage of said contaminated glycol solutions through a column or adsorber of magnesite containing activated carbon, thus minimizing the pH drop associated with a change in carbon type or the installation of a fresh carbon supply.

DETAILED DESCRIPTION OF THE INVENTION

As used herein, the term "glycol solutions" includes ethylene glycol, diethylene glycol, triethylene glycol, tetraethylene glycol and mixtures thereof. The preferred glycol solution employed in the liquid-liquid extraction manufacture of petrochemicals is tetraethylene glycol. The term "glycol solutions", as used herein, also includes aqueous mixtures of the glycols indicated above.

The term "standard activated carbon(s)" as used herein refers to those carbons which typically are: non-impregnated, hard, dense, generally coal based, but also including coconut and wood based activated carbons. Examples include; Westvaco WVL, WVG; Darco Hydrodarco 3000, 4000; Carborundum 830, 840 and the Pittsburgh Carbons; SGL, CAL, BPL, APC, APA, F-400, CPG and CPIVA.

The term "magnesite" as used herein refers to "synthetic magnesite" or magnesium oxide (MgO). Magnesite also includes the so-called "dead-burned" magnesites, Cape May, Chewelah High Grade and Brown Pebble, which are at least 80% MgO in composition. A magnesite containing carbon includes those carbons impregnated with MgO by way of a physical mixture during the manufacturing process or via aqueous solution impregnation of a magnesium salt followed by calcination. Useful MgO impregnated carbons are described in Sinha, U.S. Pat. Nos. 4,125,482 and 4,150,045 which are herein incorporated by reference. Generally, a carbon impregnated with up to about 15% by weight MgO, based upon the weight of carbon is useful in the present process, but it is anticipated that the amount of MgO that may be impregnated on activated carbon may be greater, subject to requirements of hardness, abrasion resistance and the like.

In the following Example, a number of standard activated carbons have been compared for their effect on the pH of a contaminated tetraethylene glycol solution with a magnesite containing activated carbon, Cane CAL. Cane CAL is available from Calgon Corporation, Pittsburgh, Pa., and is generally used in the purification of cane sugar liquors. Cane CAL typically contains from 5 to 10% magnesite. Cane CAL carbon is described as having pH controlling ability in sugar solutions. However, the ability to control pH in a sugar liquor purification scheme does not obviate the minimizing of pH drop in a petrochemical glycol scrubbing solution. The carbon is described in Gillmore et al., U.S. Pat. No. 2,822,304 and *Product Bulletin* No. 23-76, Calgon Corporation which are herein incorporated by reference.

As described above, isotherm studies indicate that adsorption of color causing impurities from glycol scrubbing solutions are generally best at a solution pH of 6.0 or greater. It is therefore preferred that the magnesite containing carbon employed in the present process cause a pH drop to not lower than 6.0.

EXAMPLE

Batch treatment studies were run on a contaminated sample of tetraethylene glycol scrubbing solution using six standard activated carbons, and two samples of a magnesite containing carbon. These carbons are all commercially available from Calgon Corporation, Pittsburgh, Pa. The glycol solution contained unidentified color-causing extraneous hydrocarbons.

Forty grams of each pulverized carbon were added to separate 500 ml flasks containing 200 cc of the glycol. The flasks were agitated for one hour with the use of a wrist-action shaker, maintained at a temperature of 200° F., then the mixture was filtered to remove the carbon. The pH of each filtrate was measured to determine the carbon effect in the glycol. This data is shown below in Table I.

TABLE I

Batch Study Data
Carbon Effect on Glycol pH

| Type Carbon | Grams Carbon (g) | Volume of Glycol (cc) | Temp. °F. | Contact Time (hrs.) | Filtrate pH |
|---|---|---|---|---|---|
| APC | 40 | 200 | 200 | 1 | 4.75 |
| APA | 40 | 200 | 200 | 1 | 3.14 |
| F-400 | 40 | 200 | 200 | 1 | 4.97 |
| CPG | 40 | 200 | 00 | 1 | 3.34 |
| BPL | 40 | 200 | 200 | 1 | 5.06 |
| CPIVA | 40 | 200 | 200 | 1 | 4.76 |
| Cane CAL (1) | 40 | 200 | 200 | 1 | 6.57 |
| Cane CAL (2) | 40 | 200 | 200 | 1 | 6.59 |
| Blank[1] | — | 200 | 200 | 1 | 7.08 |
| Blank[1] | — | 200 | 200 | 1 | 7.54 |
| As is[2] | — | 200 | — | — | 7.50 |
| As is[2] | — | 200 | — | — | 7.69 |

[1]Blank - heat treated glycol sample.
[2]As is - sample aliquot of glycol at room temperature.

As shown in Table I, all of the filtrates exhibited significant drops of pH as a result of carbon dosage except Cane CAL. The two acid washed carbons, APA and CPG showed the largest pH drop (3.14 and 3.34). This may be traced to the fact that acid washed carbons, if not neutralized completely, can exhibit initially low contact pH's. BPL carbon had the least pH reduction for standard carbons in the initial batch tests at 5.06. CPIVA carbon exhibited a substantial pH drop to 4.76. The Cane CAL carbon showed a very slight decrease in the pH from pH 7.08 in the blank to about pH 6.58 in the carbon treated samples.

As the data in Table I clearly shows, standard activated carbons cause a large drop in glycol pH. Magnesite containing carbon minimizes this problem. Therefore, the use of a magnesite containing carbon such as Cane CAL carbon should resolve the pH problem in a glycol scrubbing solution.

What is claimed is:

1. In the purification of contaminated glycol scrubbing solutions used in a liquid-liquid extraction process for the manufacture of petrochemicals by passage of said glycol solutions through an activated carbon filter, the improvement comprising minimizing glycol pH reduction by: employing a magnesite containing activated carbon.

2. The improved process of claim 1 wherein the pH reduction of the glycol solution is to not less than 6.0.

3. The improved process of claim 1 wherein the magnesite containing activated carbon is up to 15.0 weight percent MgO based on the weight of activated carbon.

4. The improved process of claim 1 wherein the magnesite containing activated carbon is from about 5 to 10 weight percent MgO.

5. The improved process of claim 1 wherein the magnesite containing activated carbon is from about 5 to 10 weight percent dead-burned magnesite.

6. The improved process of claim 1 wherein the magnesite containing activated carbon is from 0.1 to 5.0 weight percent MgO.

7. The improved process of claim 1 wherein the magnesite containing activated carbon is from 0.1 to 5.0 weight percent dead-burned magnesite.

* * * * *